United States Patent
Gavronsky

(10) Patent No.: US 7,155,287 B2
(45) Date of Patent: Dec. 26, 2006

(54) DEVICE FOR PERCUTANEOUS NERVE STIMULATION

(76) Inventor: Stas Gavronsky, Robert Coch Str. 27, Wayland, MA (US) 01778

( * ) Notice: Subject to any disclaimer, the term of this patent is extended or adjusted under 35 U.S.C. 154(b) by 134 days.

(21) Appl. No.: 11/078,765

(22) Filed: Mar. 14, 2005

(65) Prior Publication Data
US 2006/0206164 A1    Sep. 14, 2006

(51) Int. Cl.
*A61N 1/04* (2006.01)

(52) U.S. Cl. ........................ 607/46; 607/115; 607/149; 128/907

(58) Field of Classification Search ................ 128/907; 607/149, 115, 46, 2; 606/129
See application file for complete search history.

(56) References Cited

U.S. PATENT DOCUMENTS

| | | | |
|---|---|---|---|
| 5,074,847 A * | 12/1991 | Greenwell et al. | 604/174 |
| 6,231,548 B1 * | 5/2001 | Bassett | 604/174 |
| 6,549,810 B1 | 4/2003 | Leonard et al. | |
| 6,560,491 B1 * | 5/2003 | Leonard et al. | 607/116 |
| 6,701,190 B1 | 3/2004 | Gliner | |

OTHER PUBLICATIONS

U.S. Appl. No. 10/068,826, filed 2002 S. Gavronsky.
U.S. Appl. No. 10/962,299, filed 2004 Gavronsky et al.
http://www.library.ucla.edu/libraries/biomed/his/painexhibit/panel6.htm The Gate Control Model Opens a New Ara in Pain Research (regarding Melzack and Wall).
American Journal of Pain Management. vol. 12, No. 4, Article by Ong and Ho.
http://www.ampainsoc.org/pub/bulletin/mar99/pens.htm. Ahmed, Craig, White & Huber, 1998 Percutaneous Electrical Nerve Stimulation (PENS): A Promising Alternative-Medicine Approach to Pain Management.

* cited by examiner

*Primary Examiner*—Robert Pezzuto
*Assistant Examiner*—Shevon Johnson

(57) ABSTRACT

The present invention provides a novel device for portable percutaneous electrical nerve stimulation and electro-acupuncture. In the preferred embodiment, the device consists of a needle/electrode holder that has a linear electrode/needle guide channel and a power supply channel that intersects with the needle/electrode guide channel and serves for insertion of a pin electrode from an electrical generator (PENS unit). The pin electrode will provide an electrical contact with the needle and at the same time function as means for securing the needle in a desire position in the guide channel. The needle remains straight and the extended portion thereof is kept out of contact with the patient's skin.

8 Claims, 8 Drawing Sheets

DEVICE FOR PERCUTANEOUS NERVE STIMULATION

CROSS-REFERENCE TO RELATED APPLICATIONS

The present patent application is related to pending U.S. patent application Ser. No. 10/962,299 filed by the same applicant on Oct. 9, 2004

BACKGROUND OF THE INVENTION

1. Field of the Invention

The present invention relates to the field of electrical therapy for treating pain and other conditions, in particular to electro-acupuncture and percutaneous electrical nerve stimulation therapy. The present invention is more specifically directed to a method and device capable of delivering continuous pain relief through percutaneous electrical nerve stimulation both in and out of clinic.

2. Prior Art

Electrical therapy has long been used in medicine to treat pain and other conditions. One of the forms of electrical therapy is Transcutaneous Electrical Nerve Stimulation (TENS). The TENS method is based on a hypothesis of Melzack and Wall from 1965. They proposed that activity in coarse, afferent nerve fibers (A-beta-fibers that convey pressure, touch, and vibration) inhibits impulse transmission in pain pathways at spinal cord level. The coarse nerve fibers have a low threshold for electrical stimulation and are therefore simple to activate by stimulation using electrodes placed on the skin. Usually stimulation frequencies of 2–120 Hz are used for conventional TENS. Electro-acupuncture is another example of electrical therapy, which has been used successfully for a number of years. Current U.S. patent application Ser. No. 10/068,826 submitted by the same applicant on Feb. 11, 2002 describes an improved electro-acupuncture device.

In recent years, Percutaneous Electrical Nerve Stimulation (PENS) has been used and investigated for the management of acute and chronic pain syndromes. PENS is a new analgesic therapy that combines advantages of both electro-acupuncture and TENS. PENS therapy utilizes acupuncture-like electrodes placed in the soft tissues to stimulate peripheral sensory nerves at the dermatomal level corresponding to a local pathology. TENS, on the other hand, is a procedure that involves electrical stimulation on the surface of the skin through cutaneous electrode pads. Electro-acupuncture is similar to PENS except that it is influenced by acupuncture theory of the meridians, energy channels, and their distribution for a choice of sites to be stimulated with electricity. In modern medical acupuncture stimulation sites are chosen from both meridian and neurological considerations. A difference between PENS and TENS electro-acupuncture from the physiological perspective is well described in the American Journal of Pain Management Vol. 12 No. 4 by Ong and Ho. The article shows differences and similarities in mechanisms of pain interruption between TENS and acupuncture/electro-acupuncture along the ascending nociceptive pathways, namely, at peripheral, spinal segmental, supraspinal, and cortical levels. On peripheral level electro-acupuncture stimulates mainly the pinprick Adelta and small type III fibers for its effect. TENS stimulates mainly the tactile Abeta and large type I fibers for its effect. On the spinal level electro-acupuncture's effect is mediated via the inhibitory enkephalinergic stalked cells in lamina II of the spinal grey matter. TENS's effect is mediated via interneurons with GABA receptors in the spinal cord and this stimulates the inhibitory neurons. On the supraspinal level electro-acupuncture activates pituitary mechanisms releasing enkephalins and produces analgesia throughout the body. Conventional TENS are mostly segmental not involving pituitary mechanisms, and the analgesic effect is only segmental.

In clinic both electro-acupuncture and PENS seem to be significantly more effective than TENS. Ghoname and colleagues conducted a randomized, controlled, crossover study to compare effectiveness of PENS, TENS, and exercise therapy in 60 patients with chronic low back pain secondary to degenerative disc disease. The authors described the PENS as a therapy that combines the advantages of TENS and those of electro-acupuncture. Compared with sham PENS, TENS and exercise therapy, PENS was more effective in improving function, pain, physical activity, and quality of sleep. PENS therapy was preferred by 91% of the patients.

PENS therapy has been found to be effective in the management of pain associated with a number of conditions, including acute herpes zoster (Ahmed, Craig, White, Ghoname et al., 1998), the prevention and treatment of migraine headaches after electroconvulsive therapy, cancer pain secondary to bone metastases (Ahmed, Craig, White, & Huber, 1998). Compared with dorsal column stimulation, the PENS technique is less invasive, less costly, and less risk ridden. Electro-acupuncture has been also found effective for many conditions including, but not limited to, Irritable Bowel Syndrome and dysmenorrhea.

Currently, a PENS procedure is performed in clinic by a pain specialist, typically, by physiatrist, anesthesiologist, or acupuncturist. Patient is usually prone on the treatment table, when two or more needles/electrodes are inserted in the back and around the spine according to the location of pain. Electrodes are kept in place for 30 min to 1 hour, while being stimulated with alternating electrical current generator at frequencies typically from several to 100 Hz. Since the electrical resistance of the skin is short-circuited by the inserted electrodes, and the actual electrical current through the electrodes is very small (in milli-amperes range), the electrical stimulator can operate for a long time from a single 9V battery. These electrical devices are currently available as electro-acupuncture machines. They offer variable frequencies, intensities, and one or multiple outputs. Needle electrodes are inserted perpendicular to the skin at variable depths, depending on the area, patient's anatomy, and the etiology of pain, anywhere from several millimeters to several centimeters. Electrical clips with electrical wires are attached to the electrodes before the electrical stimulator is turned on. An example of the improved electrodes can be found in aforementioned U.S. patent application Ser. No. 10/068,826 filed by one of the s of the present application on Feb. 11, 2002. There have been many attempts to improve the electrodes and to find ideal stimulating modes (frequencies and intensities) for PENS in prior arts. Examples can be found in U.S. Pat. No. 6,549,810 issued to Paul Leonard et al. in 2003 and U.S. Pat. No. 6,701,190 issued to Brad Gliner in 2004.

While there are some differences in electrode design, duration of the procedure, and frequency modes between PENS procedures, several characteristics have remained the same in all prior arts. Namely, electrodes/needles are inserted perpendicular to the body and the external parts of the electrodes protrude above the skin. The patient has to be stationary on the table during the duration of the procedure, for 30 to 60 minutes. Also, treatment can be only repeated during patient's next visit to a pain clinic.

In order to overcome the aforementioned disadvantages of the prior art, the applicant developed a principally novel method and a device for percutaneous electrical nerve stimulation and electro-acupuncture. The new method and device are disclosed in pending U.S. patent application Ser. No. 10/962,299 filed by the same applicant and are based on inserting the needles/electrodes into the prescribed acupuncture/trigger points at slant angles so that the external parts of the needles/electrodes can be secured against the skin of the patient. The new method and device allow the use of different types of percutaneous electrodes and angular or perpendicular insertions, as long as the external parts of electrodes are in flush with the patient's skin. An angular insertion of the needles/electrodes, however, has significant advantages over perpendicular insertion in case of PENS. First, the inclined position of the needle provides distribution of current over a larger area of the patient's tissues for the same depth of insertion since the inserted part of the needle is longer in the inclined position than in the perpendicular position. Second, as the projecting part of the needle is secured to the surface of the skin, a patient is not restrained by the needles and may have freedom of motion. In other words, after insertion of the needles the patient may leave the clinic and may not be bound to the clinic during subsequent usage of the device.

However, experience showed that patients experience some discomfort. Furthermore, the known device exhibits some difficulty in use and precision control of the procedure because it is impossible to change a position of the inserted electrode in the body without compromising needle's sterility or without removing the whole electrical assembly. This is because the needle/electrode is kept in flash with the skin under an adhesive electrode. Furthermore, when a needle is used as an electrode, it should be bent after insertion so that the axis of insertion does not coincide with the axis of the needle in the inserted state. Therefore, the deformed needle tends to straighten out and to overcome the bending force, and special measures, such as an adhesive pad are needed for retaining the exposed part of the needle in a bent state and in contact with the patient's skin. When a patient that carries needles with the projecting portions held in contact with the skin by adhesive pads moves, these movements may disconnect the adhesive pads so that the projecting ends of the needles will straighten out and become unrestricted for movements. This may loosen the part of the needle inserted into the skin and even lead to extraction of the needle from the skin because of friction contact of the needle handle with the patient's clothes.

SUMMARY OF THE INVENTION

It is an object of the invention to provide a device for percutaneous nerve stimulation that allows positioning and securing of the non-inserted part of the needle/electrode at an acute angle with the patient's skin and along the same axis with the inserted portion of the needle/electrode, so that the needle does not bend excessively at the skin surface, while staying close to it. A further object is to provide the aforementioned device of the type that allows change in a position of the inserted electrode in the body without compromising needle's sterility or without removing the whole electrical assembly. It is another object to provide a device for percutaneous nerve stimulation without contact of the needle with the patient's skin at an inclined position of the needle to the patient's skin. It is still another object to eliminate development of an elastic force in the needle during the use. It is a further object to provide the aforementioned device that allows a patient to have freedom of movements during percutaneous electrical nerve stimulation procedure without a risk of loosening the needle in the patient's skin or extracting the needle during patient's movements.

The present invention provides a novel device for portable percutaneous electrical nerve stimulation and electro-acupuncture. Unlike the existing device for portable percutaneous electrical nerve stimulation by the same applicant where an external part of the needle/electrode is kept in flush with the patient's skin after the needle is inserted at an acute angle, in this new device, the external part of the electrode is aligned with the rest of the needle and stays at an acute angle to the skin after the insertion. This eliminates a bent in the body of an electrode/needle at the point of its insertion into the skin and a consequent development of an elastic force that tends to straighten out the deformed needle. In the preferred embodiment, the device consists of a needle/electrode holder that has an electrode/needle guide channel and a power supply channel that intersects with the needle/electrode guide channel and serves for insertion of a pin electrode from an electrical generator (PENS unit). The pin electrode will provide an electrical contact with needle and at the same time function as means for securing the needle in a desire position in the guide channel.

DETAILED DESCRIPTION OF THE INVENTION

Figure 1:
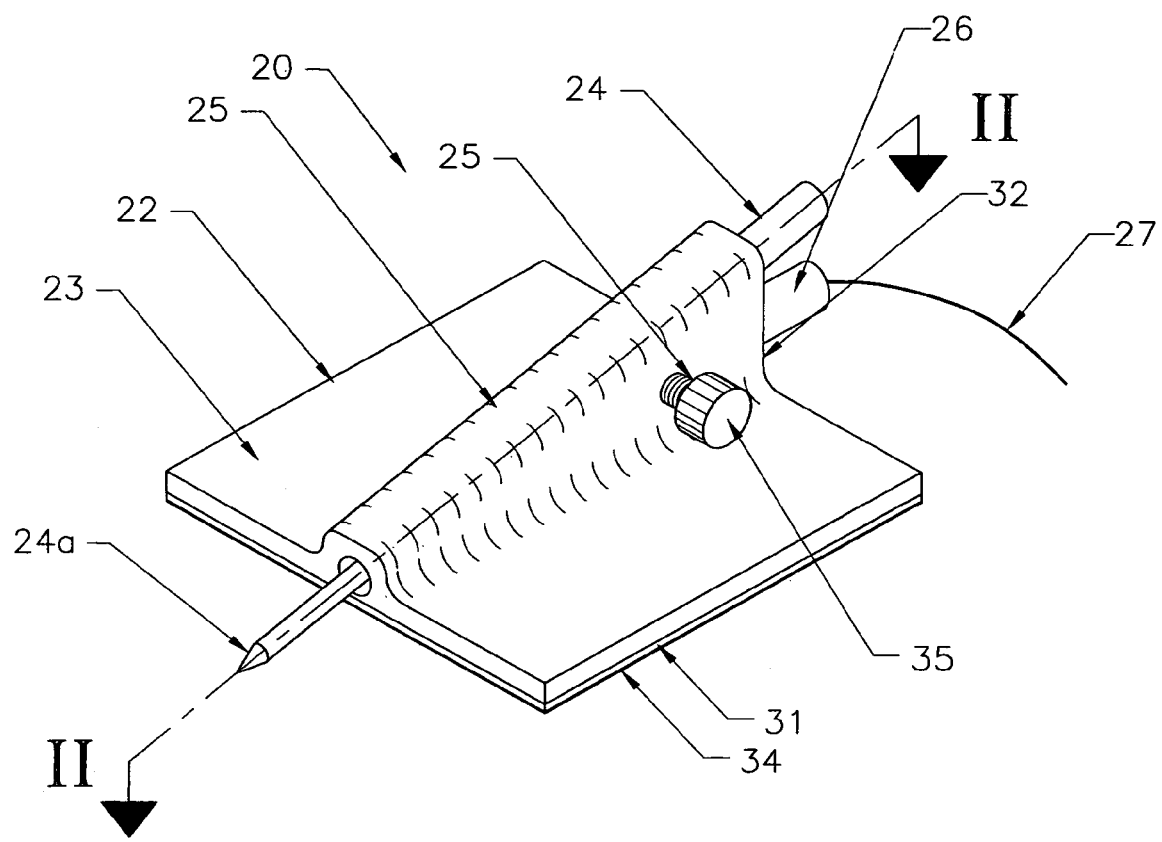
FIG. 1 is a three-dimensional view of a device for percutaneous nerve stimulation in accordance with one embodiment of the invention.
Figure 2:
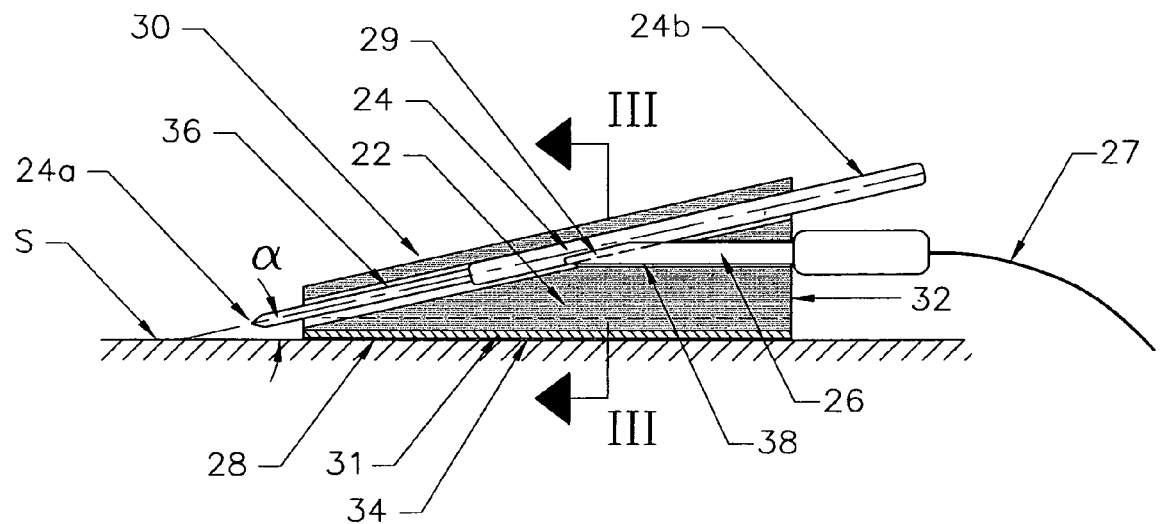
FIG. 2 is a sectional view of the device of FIG. 1 along the line II—II.

A device 20 for percutaneous nerve stimulation according to one embodiment of the invention is shown in FIG. 1, which is a three-dimensional view. FIG. 2 is a sectional view of the device along the line II—II. The device 20 is comprised of a needle/electrode holder 22, a needle/electrode 24, and a terminal pin 26 for supply of power to the needle/electrode 24.

As can be seen from FIGS. 1 and 2, the needle/electrode holder 22 is comprised of a plate-like base 23 with a ridge 25 in the middle of the base 23. The ridge extends in the direction coaxial with the direction of insertion of the needle/electrode. The needle/electrode holder 22 has a triangular cross section in the direction of line II—II shown in FIG. 1. It has a flat bottom side 28 (the side of the triangle opposite to the hypotenuses), an inclined upper side 30 of the ridge 25 (the hypotenuses of the triangle), and a second non-hypotenuses side 32 of the ridge, the direction of which is not critical. The needle holder 22 may be made from a non-conductive material or conductive material. Preferably, it is a resilient material such as rubber or the like that can accommodate slight deformations associated with movements of the patient's body when the needle holder is attached to the patient's skin, e.g., by means of a double-sided adhesive pad 34, one side of which is attached to the flat bottom side 28 and another to the patient's skin S (FIG. 2). When the needle/electrode holder 22 is made from a conductive material, the needle/electrode 24 should be electrically connected to the pulse generator (not shown in FIG. 1), while the needle/electrode holder 22 should be attached to the patient's skin S via an insulation layer 31 located between the holder's bottom 28 and the adhesive pad 34. If necessary, the insulation layer 31 on the bottom side 28 can be attached to the patient's skin S directly with glue without the use of the intermediate adhesive pad 34.

The needle/electrode holder 22 has a through channel 36 (FIG. 2) which is inclined at an acute angle α (FIG. 2) to the bottom side 28, preferably parallel to the hypotenuses side 30. This channel is intended for insertion and guiding the aforementioned needle/electrode 24 and is inclined towards the point of insertion of the needle/electrode 24 into the patient's skin S. The angle α between the base plane and the axis of the ridge 25 can be anywhere from several to 60°. The needle/electrode has a needle portion 24a, the tip of which is intended for insertion into the patient's skin S, and a handle portion 24b that protrudes outside from the needle holder 22. The diameter of the channel 36 should be slightly greater than the cross-sectional diameter of the handle portion 24b.

Figure 3:
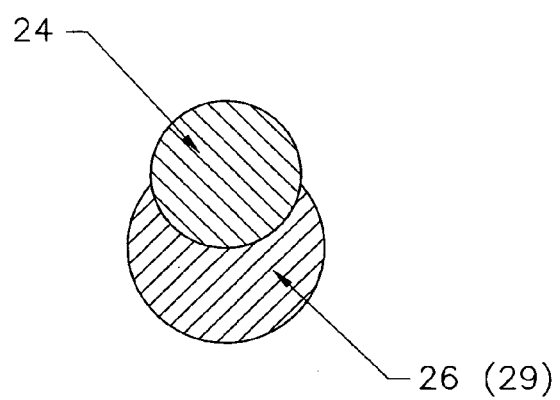
FIG. 3 is a sectional view along the line III—III of FIG. 2.

In order to provide electrical contact of the conductive part of the needle/electrode 24 to aforementioned terminal pin 26 that is connected to a power source (not shown), e.g., an alternating electrical current generator of the type described in aforementioned U.S. patent application Ser. No. 10/962,299 for generating pulse signals, e.g., with frequency of 100 Hz and operating from a small battery, e.g., of 9V, the non-conductive needle/electrode holder 22 may be provided with another channel 38 (FIG. 2) that extends in a direction transverse to the through channel 36 and intersects therewith. The terminal pin 26 is inserted into the channel 38 till contact with the previously inserted needle/electrode 24 and may have a cross-sectional diameter that will provide a tight sliding fit for the terminal pin 26, or the pin may be positively fixed, e. g., with a screw (not shown). As shown in FIG. 3, which is a cross section along the line III—III of FIG. 2, the terminal pin 26 may have a beveled tip 29 and a cross section conforming to the cross-sectional shape of the needle/electrode 24. Reference numeral 27 designates a wire that connects the terminal pin 26 with the current generator. If necessary, the terminal pin 26 can be fixed in the needle-locking position by a fastener, e.g., a small screw 35 (FIG. 1).

Figure 4:
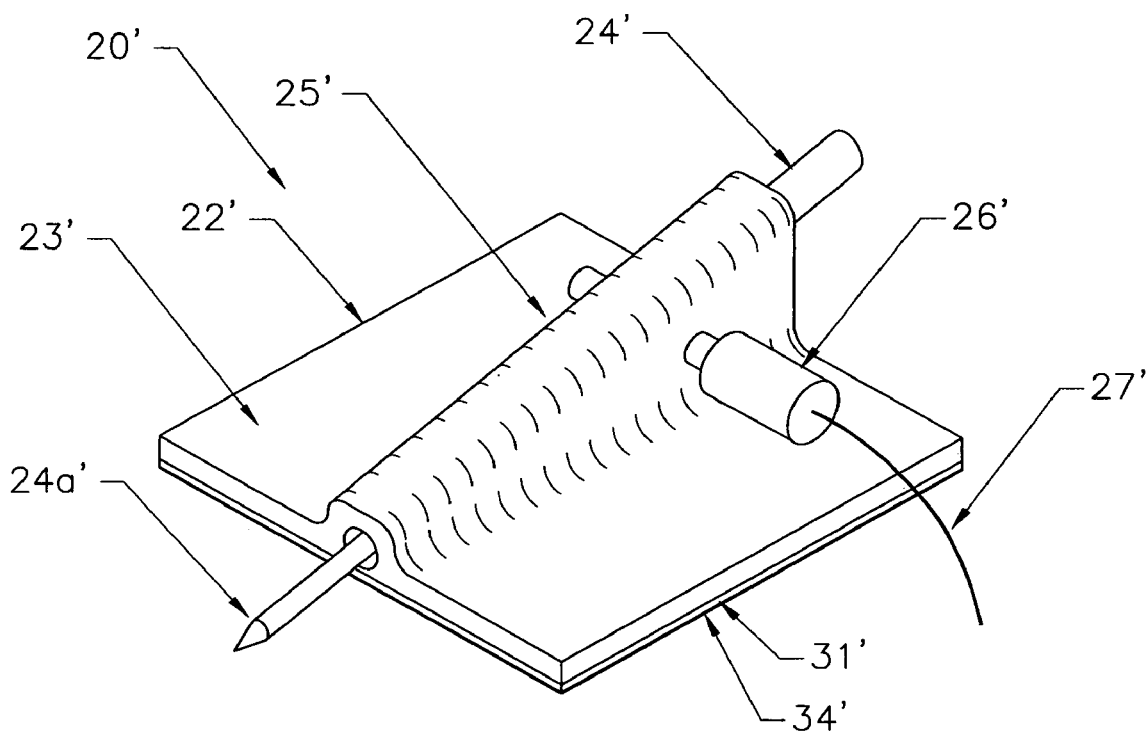
FIG. 4 is a three-dimensional view of the device similar to the one shown in FIG. 1 but for embodiment of the invention with the direction of the terminal pin substantially perpendicular to the direction of the needle/electrode.

The embodiment of the invention shown in FIG. 4, which is a three-dimensional view of the electro-acupuncture and percutaneous electrical nerve stimulation device 20' is substantially the same as the one shown in FIGS. 1–3 and differs from it by the fact that the terminal pin 26' is inserted in a channel substantially perpendicular to the direction of the needle/electrode 24'. Since the rest of the device 20' is the same as in the device of the previous embodiment, description of the other parts and elements of the device of FIG. 4 is omitted and they are designated by the same reference numerals with addition of a prime. For example, the needle/electrode is designated by reference numeral 24', etc.

Figure 5:
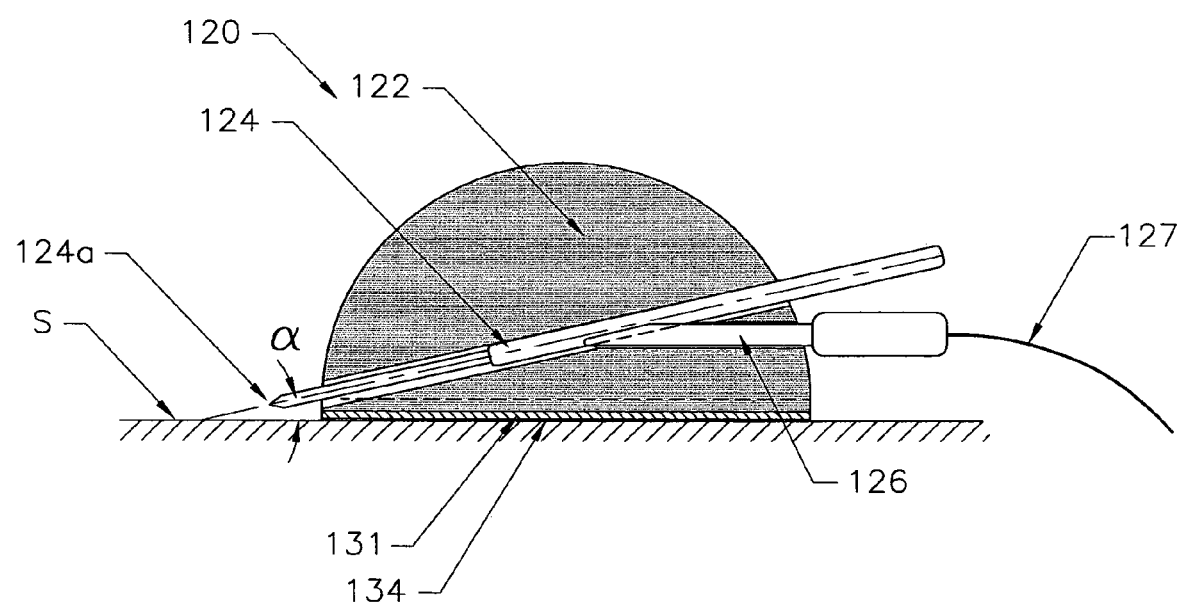
FIG. 5 is a view of the device of the invention with a semispherical shape of the needle/electrode holder.

FIG. 5 shows another embodiment of the device 120 of the invention, wherein in order to facilitate movements of the device attached to the patient's body relative to the clothes, the needle/electrode holder 122 is made in a semi-spherical shape. In a plan view such a device has a circular shape. Since the rest of the device 120 may be the same as in the device of the previous embodiment, description of the other parts and elements of the device of FIG. 4 is omitted and they are designated by the same reference numerals with addition of 100. For example, the needle/electrode is designated by reference numeral 124, etc.

Figure 6:
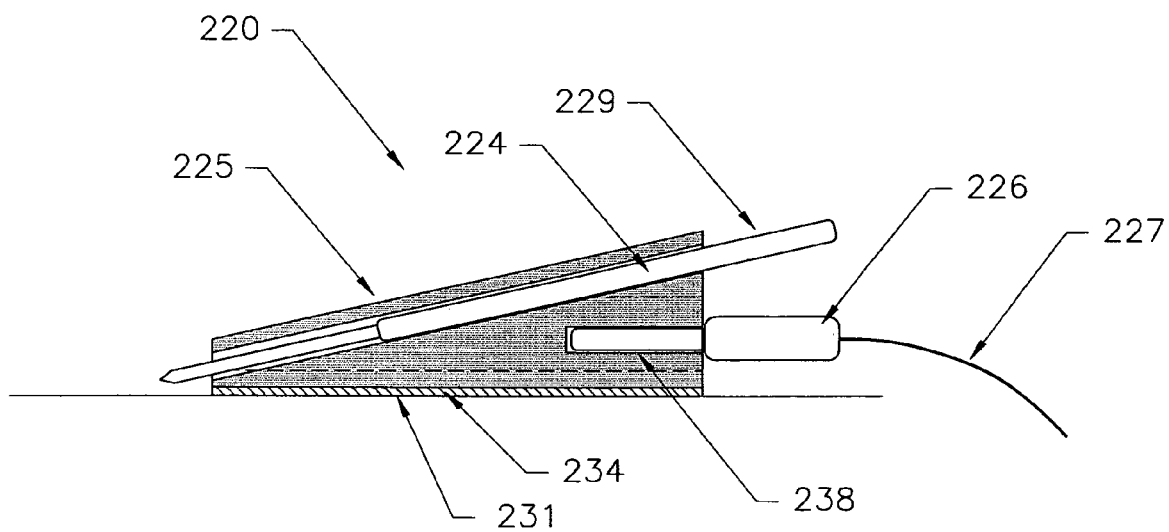
FIG. 6 is a view of the device of the invention where the needle/electrode holder is made of a conductive material and the terminal pin is inserted into a blind hole of the holder.

FIG. 6 shows a side sectional view similar to the one shown in FIG. 2 for a percutaneous nerve stimulation device 220 in accordance with still another embodiment of the invention. In this embodiment, the base 223, or at least the ridge 225, is made from a resilient electro-conductive material, e.g., a graphite-filled rubber, and the channel for insertion of the terminal pin 226 may be made in the form of a blind hole that does not reach the passage for the needle/electrode 224 that has a conductive handle 229. The rest of the device is the same as in the embodiment of FIG. 1 and is shown with parts that are designated by the same reference numeral but with an addition of 200. For example, the device as a whole is designated by reference numeral 220, the ridge is 225, etc. The bottom surface of the base 223 is covered with a layer 231 of an insulating material, which, in turn, is covered with an adhesive layer 234 for attachment to the patient's skin.

Figure 7:
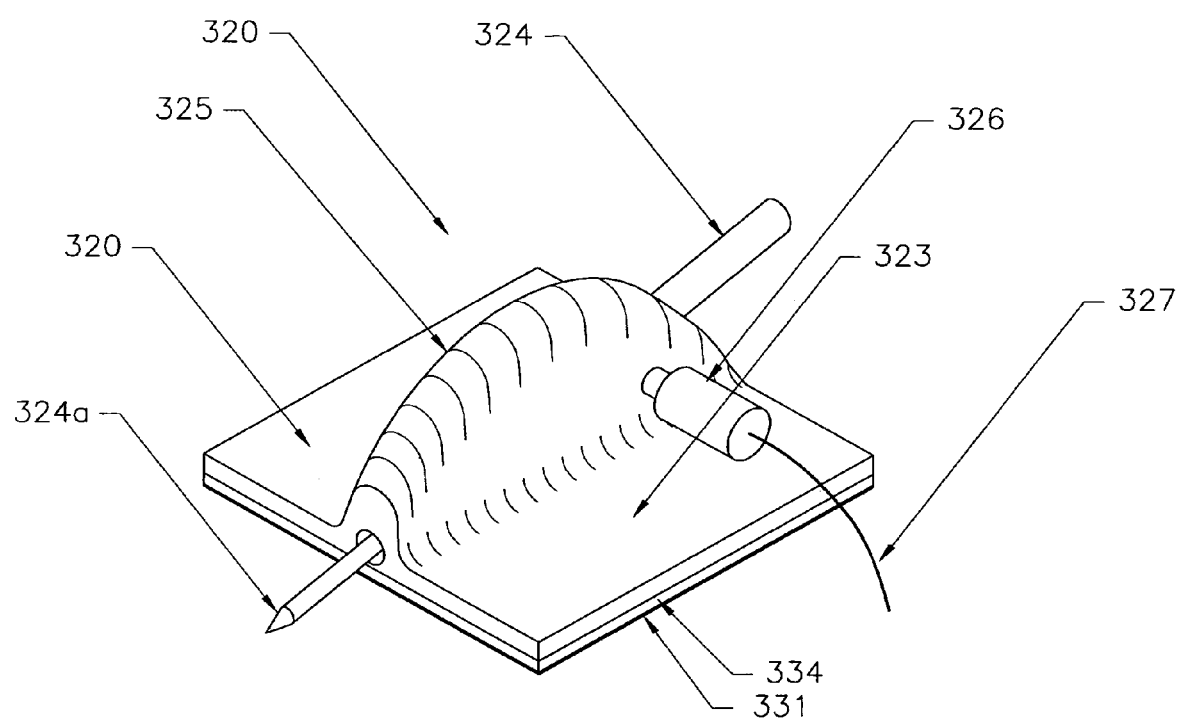
FIG. 7 is a three-dimensional view of a percutaneous nerve stimulation device in accordance with an embodiment of the invention that is similar to the embodiment of FIG. 5 but differs from it by the fact that instead of the spherical shape on the entire needle/electrode holder the streamlined shape is imparted only to the ridge.

FIG. 7 is a three-dimensional view of a percutaneous nerve stimulation device 320 in accordance with an embodiment of the invention that is similar to the embodiment of FIG. 5 but differs from it by the fact that, instead of the spherical shape on the entire needle/electrode holder 322, the streamlined shape is imparted only to the ridge 325. The rest of the device is similar to the previous embodiments, e.g., to the one shown in FIG. 4.

The identical parts are designated by the same reference numerals as in the embodiment of FIGS. 1—3 but with an addition of 300. For example, the device as a whole is designated by reference numeral 320, etc.

Figure 8:
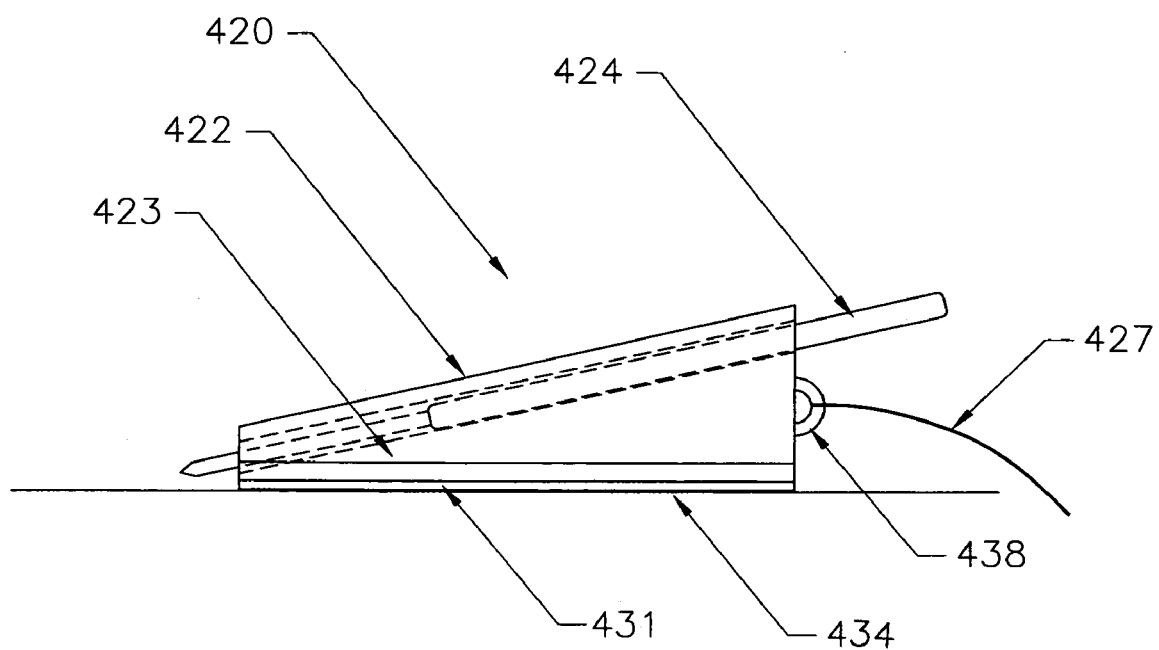
FIG. 8 is a view of the device of the invention where the needle/electrode holder is made of a conductive material and is connected by a conductive wire directly to the pulse generator.

FIG. 8 shows an embodiment of the invention for a device 420 that may have a needle/electrode holder made from a conductive material such as the one mentioned with reference to FIG. 6 and with a shape similar to any needle/electrode holder of the previous embodiments. Reference numeral 422 designates the needle/electrode holder, 423 is a base, 431 is an insulating layer, and 432 is an adhesive layer. The device of this embodiment differs in that the conductive holder 422 is connected directly to the output terminal of the pulse generator (not shown) without the use of a conductive wire 427. The wire can be connected to the conductive holder 420 by any suitable means, e.g., by soldering, or mechanically, e.g., by connecting to a perforated lug 438 molded integrally with the rest of the holder's body.

Figure 9:
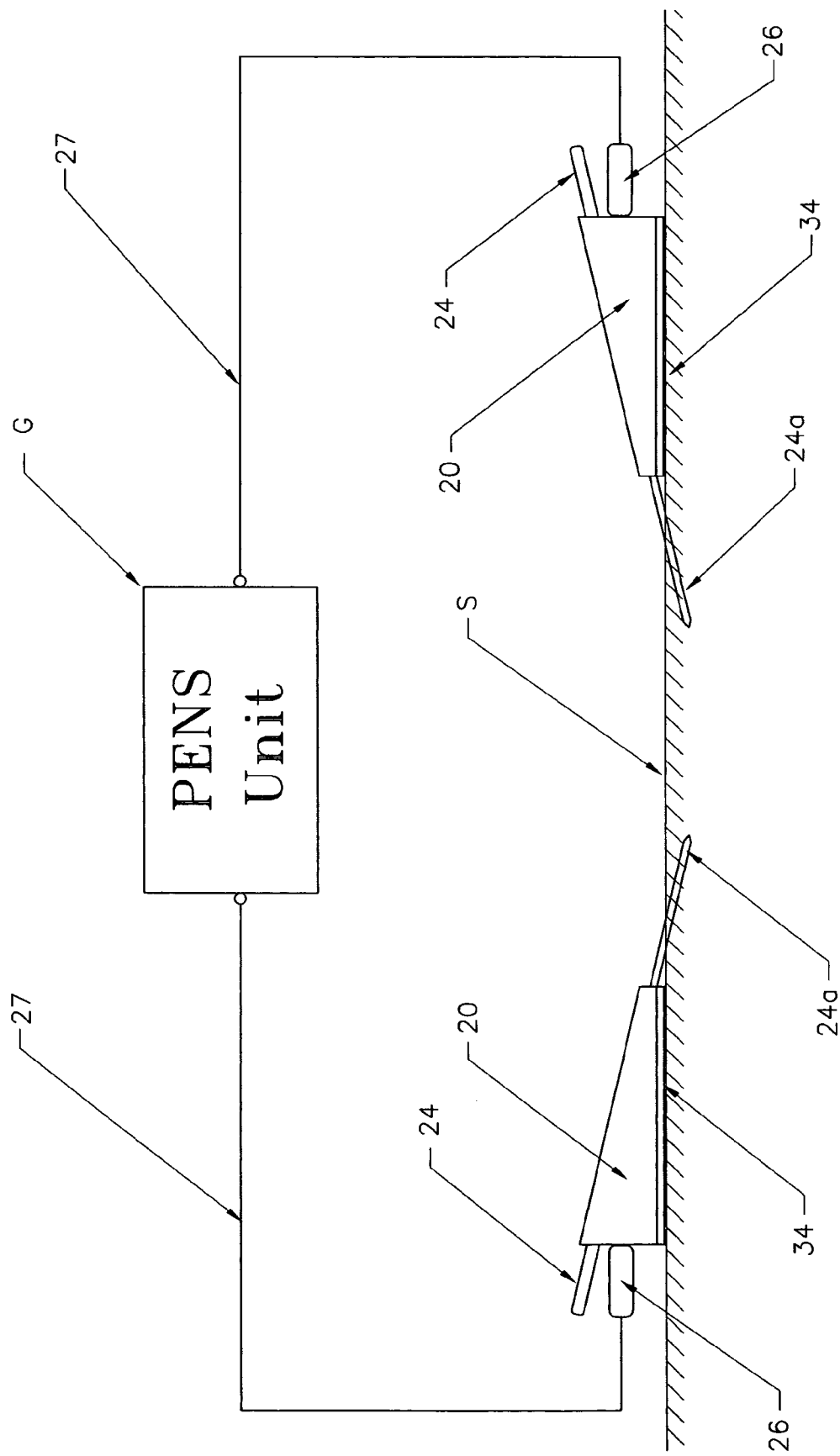
FIG. 9 is a diagram illustrating operation of the device of the invention for percutaneous nerve stimulation.

The device in operation is shown in FIG. 9. The principle of operation described below is applicable to a device of any embodiment described above. Let us assume that this is the device 20 of the embodiment shown in FIGS. 1–3. At least two aforementioned devices are typically used for the electro-therapeutic procedure (FIG. 9). The devices 20 are attached to the patient's skin S at a predetermined distance selected by the practitioner in accordance with the procedure. The devices are secured in place, e.g., with the use of an adhesive layer 34 at the bottom of the base 22, the tips 24a are inserted into the patient's skin to a required depth at an acuter angle α (FIG. 2) by guiding the needle/electrode 24 along the guide channel 36. Positions of the needle/electrodes are fixed by terminal pins 26 inserted into the respective channels 38 till contact with the conductive parts of the needle/electrodes 24 and connected to the pulse generator G (FIG. 9).

After the electrical circuit of the system shown in FIG. 9 is complete and the needle/electrodes 24 are fixed in their operative positions, the practitioner makes sure that the patient's movements are unrestricted and that there is no discomfort from the inserted needles/electrodes, or from the adhesive tapes. At this moment the PENS procedure can be tested. When the generator G is activated, the tissues between two devices 24, more specifically, between the tips 24a of the inserted electrodes/needles 24, represent the electrical load of the PENS unit. The generator G is turned on, either by using the remote control 50, or by a local switch (not shown). The electrical current starts flowing through the electrical wires 27 (FIGS. 1, 2, 8) into the needles/electrodes 24, 24 and through the patient's tissues located between the tips 24a, 24a of the two needles/electrodes 24, 24. The current is slowly adjusted from low to high until the patient feels a tolerable amount of stimulation. The electrical parameters, which include intensity and frequency (usually 2 to 100 Hz) are selected according to the patient's diagnosis and his/her tolerance level and are tested while the patient is still in the office. The patient is instructed how to use the system away from the office and how to remove the needles/electrodes 24, 24 when desired. As in an assembled state the height "h" (FIG. 1) of the electrode assembly 20 over the patient's skin does not exceed 8 mm, the patient does not experience any restriction of movements while carrying the device on his/her body.

Alternatively, the patient is offered to come back to the office after certain period of time, say, by the end of the same day, after having used the device at work for a number of hours on and off, and to have it removed by a health care provider. The portable electro-acupuncture device of the invention is capable of providing multiple therapeutic PENS sessions in a course of one day for the same patient in order to control pain without extra participation of a health care provider. The number of the therapeutic sessions and their modes, such as the intensity of the electrical current, frequency, and duration of each session can be pre-programmed by a therapist or controlled manually by the patient according to the patient's needs.

The main advantage of the new device 20 is its portability, as well as greater reliability, convenience and safety. In prior art by the same applicant (patent pending), it is impossible to change a position of the inserted needle/ electrode 24 in the body without compromising needle's sterility or without removing the whole electrical assembly, since the needle/electrode is kept in flash with the skin under an adhesive electrode. An ability to easily change needle's position without disassembling the device 20 is a great advantage. For example, withdrawing a needle 24 slightly at the site of insertion can provide just enough comfort for a patient to perform certain physical activities, such as walking or exercising, or can help to resolve a muscle cramp which might have developed in response to mechanical and/or electrical stimulation. Later, the needle 24 can be placed deeper as required by a protocol. To change the needle position in the preferred embodiment of the device, one releases the pin electrode 26 first, then, using the protruding portion of the handle 24b (FIG. 2), changes position of the needle 24 as desired, either by withdrawing it or pushing it deeper, and, then, secures the needle in a new position by re-introducing the pin back into its original tight state. Another significant advantage of the new device 20 is an ability to keep a needle straight during portable PENS. It eliminates upward pull of the inserted portion of the needle due to the bent in the body of the needle, which exists in prior art. Although the above advantages were mentioned specifically for the embodiment of FIGS. 1–3, they are applicable to the devices of all other embodiments as well.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For examples, the base of the needle/electrode holder may have any suitable shape such as round, square, rectangular, triangular, hexagonal, etc. The entire needle/electrode holder may have any streamline shape. In the triangular cross section of the ridge, the non-hypotenuses sides are not necessarily perpendicular to each other. The needle/electrode holder can be made from any suitable materials such as plastics, etc. The wires linked to the pulse generator can be connected by any means and to any part of the conductive needle/electrode holder.

What I claim is:

1. A device for percutaneous nerve stimulation by inserting a tip of a needle/electrode connected to a source of electric pulses into a selected point on the skin of a patient, comprising:
    a needle/electrode holder having an outer surface and a bottom surface for placement on the skin of said patient;
    attachment means on said bottom surface for attachment to said skin;
    a through channel formed in said needle/electrode holder, said through channel being inclined at an acute angle to said bottom surface with inclination towards said selected point;
    a needle/electrode inserted into said through channel;
    a source of electric pulses;
    a terminal pin channel that has a tip and extends from said outer surface of said needle/electrode holder to said through channel; and
    a terminal pin connected to said source of electric pulses and inserted into said a terminal pin channel till electrical contact of said tip with said needle/electrode,
    wherein said tip of said terminal pin that is in contact with said needle/electrode is beveled to conform the shape of said needle/electrode in the area of contact.

2. The device of claim 1, wherein said terminal pin channel is substantially in the same plane with the said needle-electrode, said plane being substantially perpendicular to said bottom surface.

3. The device of claim 1, wherein said needle/electrode holder comprises a base plate that has said bottom surface and a ridge portion on the side opposite to said bottom surface, said through channel passes through said ridge portion and wherein said terminal pin channel is substantially in the same plane with the said needle-electrode, said plane being substantially perpendicular to said bottom surface.

4. The device of claim 3, wherein said terminal pin is substantially perpendicular to said needle-electrode.

5. The device of claim 3, wherein said ridge portion has an upper surface selected from a rounded streamlined surface and a linearly inclined surface having an inclination parallel to the inclination of said through channel.

6. The device of claim 1, wherein said terminal pin is substantially perpendicular to said needle-electrode.

7. The device of claim 1, wherein said needle/electrode holder is made from a material selected from a conductive material and non-conductive material and wherein, in case of said conductive material said electrical connecting means comprises an electric conductor that electrically connects said source of electric pulses to any place of said needle/electrode holder, said needle-electrode being conductive, said device being provided with an insulation layer that isolates said conductive material from said skin, while in case of said non-conductive material said device further comprises a terminal pin that is electrically connected to said source of electric power, said needle/electrode holder has a pin guiding channel that is open to said outer surface and reaches said through channel, said terminal pin being inserted into said pin guiding channel till electrical contact with said needle/electrode, said needle/electrode being conductive.

8. The device of claim 7, wherein said conductive material and said non-conductive material are resilient materials.

\* \* \* \* \*